United States Patent [19]

Greenblatt et al.

[11] Patent Number: 5,393,404
[45] Date of Patent: Feb. 28, 1995

[54] HUMIDITY SENSOR WITH NASICON-BASED PROTON-CONDUCTING ELECTROLYTE

[75] Inventors: Martha Greenblatt, Highland Park, N.J.; Shouhua Feng, Changchun, China

[73] Assignee: Rutgers, The State University of New Jersey, New Brunswick, N.J.

[21] Appl. No.: 79,237

[22] Filed: Jun. 17, 1993

[51] Int. Cl.[6] .................... G01N 27/26; G01N 27/406
[52] U.S. Cl. .................................... 204/430; 204/153; 204/22; 204/421; 204/424; 204/427
[58] Field of Search ............... 204/430, 421–429, 204/153, 18, 153, 22; 422/98; 429/30–33, 191, 193

[56] References Cited

U.S. PATENT DOCUMENTS

| | | | |
|---|---|---|---|
| 3,276,910 | 10/1966 | Grasselli et al. | 429/33 |
| 3,776,831 | 12/1973 | Roy et al. | 204/422 |
| 4,024,036 | 5/1977 | Nakamura et al. | 204/129 |
| 4,497,701 | 2/1985 | Murata et al. | 204/430 |
| 4,587,172 | 5/1986 | Roy et al. | 428/450 |
| 4,703,023 | 10/1987 | Yamai | 501/102 |
| 4,718,991 | 1/1988 | Yamazoe et al. | 204/421 |
| 4,751,206 | 6/1988 | Yamai et al. | 501/102 |
| 4,961,957 | 10/1990 | Kawae et al. | 427/125 |
| 4,976,991 | 12/1990 | Ammends et al. | 427/125 |
| 5,133,857 | 7/1992 | Alberti et al. | 204/421 |

OTHER PUBLICATIONS

Berger et al, "Zirconium Phosphate Membranes for Intermediate Temperature Fuel Cells", *J. Electrochem. Soc.: Electrochemical Science*, vol. 45, No. 3, Mar., 1968, pp. 230–233.

*Primary Examiner*—T. Tung
*Attorney, Agent, or Firm*—Weingram & Zall

[57] ABSTRACT

A humidity sensing device comprising a solid electrolyte evidencing proton conductivity includes a composite comprising $HZr_2P_3O_{12}/ZrP_2O_7$. The humidity sensing device is operative over a temperature range from 350°–600° C.

14 Claims, 9 Drawing Sheets

HUMIDITY SENSOR WITH NASICON-BASED PROTON-CONDUCTING ELECTROLYTE

BACKGROUND OF THE INVENTION

1. Field of the Invention

The present invention relates to a humidity sensing device comprising a solid electrolyte. More particularly, the present invention relates to a humidity sensing device comprising a solid electrolyte evidencing proton conductivity and to a method for the preparation thereof.

2. Description of the Prior Art

Heretofore, the use of solid electrolyte humidity sensors as a means for monitoring or controlling the environment has been limited. These devices typically provide an electrical signal which may be potentiometric, amperometric or conductometric in nature in response to the level of humidity in the atmosphere. Among the devices proposed for this purpose are the galvanic cell type humidity sensors, which either employ proton or oxide ion conducting electrolytes as humidity sensing elements. The electromotive force evidenced by such cells typically follows Nernstian behavior which serves as a calibration curve for the sensor. The proton or oxide ion conducting solid electrolyte chosen for use in such devices then becomes the prime factor in the construction of such humidity sensors. Workers in the art selected sintered perovskite-related phases in the barium or strontium cesium yttrium oxide family $(MCe_{1-x}Y_xO_3$ [M=Ba or Sr]) for this purpose. However, studies have revealed that electronic and/or proton ion conduction in these materials results in significant deviations from Nernstian behavior, so imposing additional calibration requirements. Accordingly, workers in the art have focused their interest upon alternative materials in their quest to find humidity sensing properties which will satisfy their needs, particularly those which are operative at high temperatures in excess of 100° C.

Numerous references disclose gas sensors and humidity sensitive devices. However, none of these references disclose or suggest the specific galvanic type sensor described herein. Typical of the prior art references are the following:

Nakamura et al., U.S. Pat. No. 4,024,036, discloses a proton permselective solid-state member formed of a heteropoly acid represented by the generic formula, $H_m[X_xY_yO_z]$ $nH_2O$ or a salt thereof. In this formula, X represents at least one member selected from the group consisting of boron, aluminum, gallium, silicon, germanium, tin, phosphorous, arsenic, antimony, bismuth, selenium, tellurium, iodine and the first, second and third transition metals, Y represents at least one member selected from the first, second and third transition metals, provided that X and Y do not represent the same substance; m, x, y, z and n each represents a positive numerical value. The permselective member can be used as an electrolyte in a fuel cell and as a membrane in a hydrogen gas refining system.

Murata, et al., U.S. Pat. No. 4,497,701 discloses a humidity sensitive device comprising an insulated substrate, first and second electrodes formed on the surface of the insulating substrate and spaced apart from each other, and a humidity sensitive film formed on the surface of the insulating substrate and covering the surface of the substrate between the electrodes. It includes a conductive powder or a semi-conductive powder, a solid electrolyte powder and an organic polymer, at least part of which is cross-linked by a zirconium compound, which serves as a cross-linking agent to form a bridge to the organic polymer and to make the structure of the humidity sensitive film stable. Additionally, the zirconium compound increases the variation rate of the resistance value as a function of moisture absorption. Thus, the range of the resistance value can be made large and the humidity sensitive device can be used as a dew sensor.

Roy et al., U.S. Pat. No. 4,587,172 discloses a low i$(Na)j(Zr_{2-z}Na_{4z})$ k$(P_{3-x}Na_xSi_x)O_{12}$. This composition evidences expansion ceramic material having the molecular formula a low thermal expansion and may be used in low expansion optical reflective structures. Such structures have an optically reflecting film deposited on a ceramic substrate having a very small thermal coefficient of expansion.

Yamai, U.S. Pat. No. 4,751,206, discloses a method of making a low thermal-expansive zirconyl phosphate ceramic, $(ZrO)_2$—$P_2O_7$. The method involves sintering a fine-powder compact of zinc oxide, magnesium oxide, bismuth oxide, manganese oxide, iron oxide, cobalt oxide, or nickel oxide, at a temperature ranging from 1200° C. to 1700° C. The resulting ceramic has a low thermal expansion coefficient.

Yamazoe, et al., U.S. Pat. No. 4,718,991, relates to proton gas sensors and a method for the use thereof in detecting gasses in oxygen containing ambients. The described sensor comprises three electrodes, an ionization electrode, a reference electrode and a detection electrode, each of which is connected to a proton conductor. Upon short circuiting of the ionization and reference electrodes, a measurement of the difference of potential across the detection electrode is made, thereby indicating the presence of gas.

Yamai, et al., U.S. Pat. No. 4,751,206, discloses a low thermal expansion material, potassium zirconium phosphate. This material has high strength and high thermal shock resistance. This product may be used for furnace refractories which are subject to thermal shock and as thermal shielding materials such as protective tiles on space vehicles which shield the vehicle from the heat of re-entry to the atmosphere.

Kawae, et al., U.S. Pat. No. 4,961,957, discloses an electrochemical cell having a solid electrolyte body and a plurality of electrodes formed thereon. At least one of the electrodes is porous, for use in determining the concentration of a subject gas in an atmosphere. The porous electrode may be comprised of platinum, an alloy of platinum, or another metal such as nickel, silver, gold, rhodium, palladium, iridium or ruthenium. The solid electrolyte body used as an oxygen sensor is formed of an oxygen-ion conductive solid electrolyte which includes $ZrO_2$(zirconia) as a major component, and at least one additive such as $Y_2O_3$, CaO, $Yb_2O_3$, and MgO.

Ammende et al., U.S. Pat. No. 4,976,991, discloses a hydrogen sensor having a solid electrolyte comprised of nasicon, titsicon, khibinskite, wadeite or $\beta$-$Al_2O_3$. The electrodes are formed of platinum, palladium or palladium oxide.

OBJECTS AND SUMMARY OF THE INVENTION

An object of the present invention is to prepare a humidity sensor capable of operating at elevated temperatures.

A further object of the invention is to provide a galvanic cell type humidity sensor operative at temperatures in excess of 100° C.

Another object of this invention is to provide a humidity sensor based upon proton conductivity.

Still another object of this invention is to provide a humidity sensor evidencing high levels of reproducibility and durability.

Another object of the present invention is to provide a proton conducting solid electrolyte appropriate for humidity sensing at relatively high temperature.

Another object of the invention is to provide a proton conducting solid electrolyte humidity sensor that is selective (i.e. does not give a response when impurity gases such as ethyl alcohol, acetic acid and ammonia are present).

In accordance with the present invention these objectives have been attained while effectively obviating the limitations of the humidity sensitive devices employed heretofore.

The present invention comprises a humidity sensing device based upon a protonic Nasicon conductor comprising a galvanic cell based upon a $HZr_2P_3O_{12}/ZrP_2O_7$ composite humidity sensor operative in the range of 350°–600° C. The described sensor evidences Nernstian behavior which confines the mechanism of proton conductivity in the composite electrolyte sensor.

BRIEF DESCRIPTION OF THE DRAWINGS

The invention will be more readily understood by reference to the following detailed description taken in conjunction with the drawings wherein.

DETAILED DESCRIPTION OF THE INVENTION

The first step in the fabrication of the humidity sensor of the present invention involves preparing a $HZr_2P_2O_{12}/ZrP_2O_7$ composite. The proton substituted NASICON, $NaZr_2P_3O_{12}$, is obtained by the conventional technique of calcination of $(NH_4)Zr_2P_3O_{12}$, the latter being conveniently synthesized hydrothermally in an autoclave lined with polytetrafluoroethylene. This technique typically involves reacting an aqueous mixture of $ZrOCl_2.8H_2O$ and $NH_4H_2PO_4$. Crystallization of the mixture is then effected under autogenous pressure and the resultant crystalline product is filtered, washed and dried at ambient temperature. Thereafter, $HZr_2P_3O_{12}$ is prepared by heating the crystalline $(NH_4)Zr_2P_3O_{12}$ in air at approximately 650° C. for 5 hours. The other starting material $\alpha$-$ZrP(Zr[HPO_4]_2.H_2O)$ is synthesized by conventional techniques.

Next, $HZr_2P_3O_{12}$ (HZP) in powdered form is mixed with $\alpha$-$Zr(HPO_4)_2.H_2O$ (ZrP) in a mole ratio of unity to yield an HZP-ZrP mixture. The resultant mixture is then ground and pelletized, typically with a pressure of 150 klb/in$^2$ to yield a dense ceramic pellet. The resultant humidity sensing element is a sintered compact composite phase of $HZr_2P_3O_{12}$ and $ZrP_2O_7$ which is mechanically stable.

The resultant pellet is next sintered in air to yield a pellet having a density greater than 80% of ideal density.

The next step in the fabrication of the inventive humidity sensor involves forming electrode connections on the sintered pellet. This end is attained by coating each face of the pellet with platinum ink. Finally, the pellet, bearing platinum electrodes, is heated at approximately 600° C. for a time period of the order of 10 hours to form the desired sensor disk.

Figure 1A:
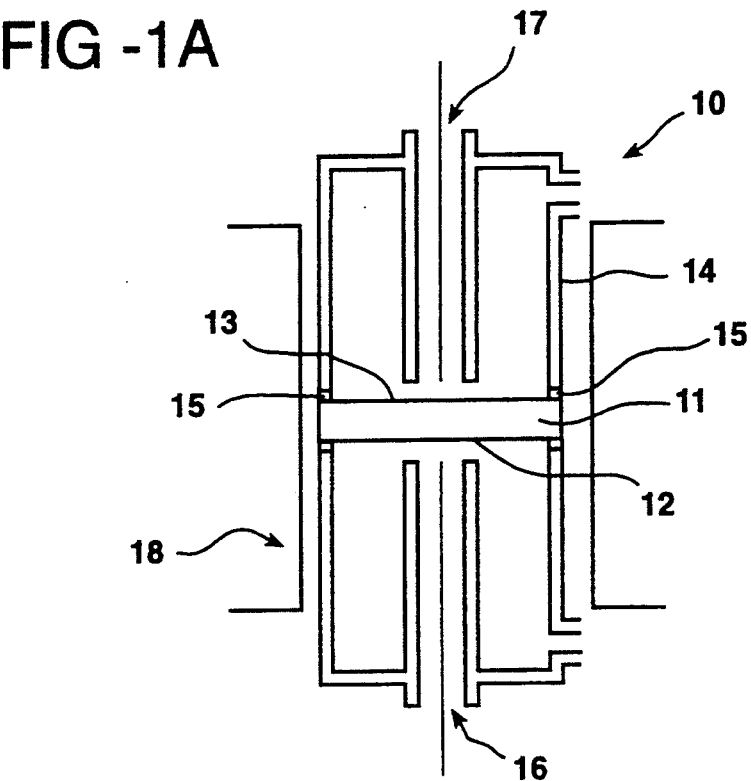
FIG. 1a and FIG. 1b are schematic representations of a galvanic type humidity sensor of the invention.

With reference now to FIG. 1A, there is shown a schematic representation of a galvanic cell 10 in accordance with the invention. Shown in FIG. 1a is a sensor electrolyte 11 comprising a $HZr_2P_3O_{12}/ZrP_2O_7$ composite humidity sensor having platinum electrodes 12 and 13 affixed thereto. Electrolyte 11 is shown disposed within quartz tubing 14 at essentially the midpoint thereof and held in place by means of ceramic sealant 15, thereby dividing the cell into two chambers, a reference gas chamber 16 and a sample gas chamber 17. In operation, cell 10 is disposed within an electric furnace 18 and humidity is introduced to reference chamber 16 and sample chamber 17 from a suitable water reservoir (not shown) using air as the carrier gas at a flow rate typically of the order of 220 cc/min. For comparative purposes, the humidity in the reference compartment is fixed at 3.16 mmHg by maintaining the reference water reservoir in an ice bath. The humidity in the sample compartment is varied by altering the temperature of the sample water reservoir.

Figure 1B:
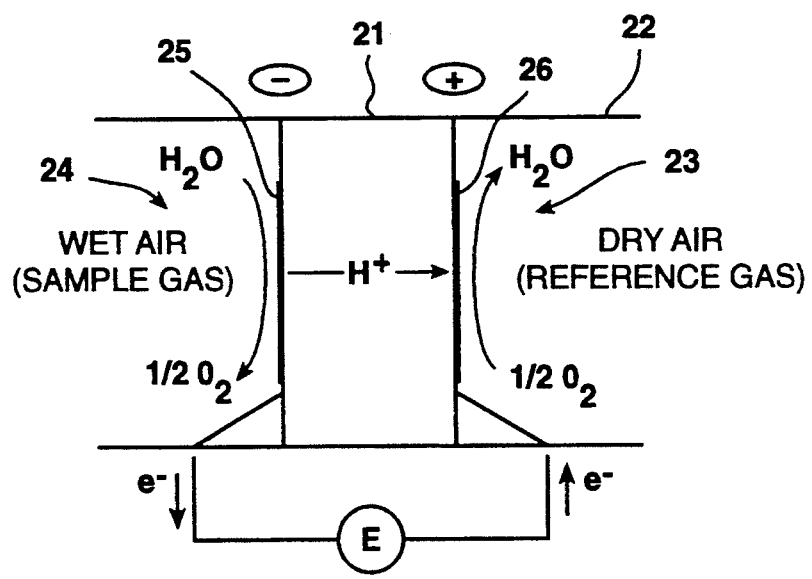

With reference now to FIG. 1b, there is shown a schematic representation of a galvanic cell assembly of the invention. Shown is proton conducting solid electrolyte 21 disposed in chamber 22 which separates the cell into reference gas chamber 23 and sample gas chamber 24. When the water vapor in chambers 23 and 24 is different, the following reactions occur at electrodes 25 and 26, respectively:

$$H_2O = 2H^+ + \tfrac{1}{2}O_2 + 2e^- \text{ (anode)} \qquad \text{Equation [1]}$$

$$2H^+ + \tfrac{1}{2}O_2 + 2e^- = H_2O \text{ (cathode)} \qquad \text{Equation [2]}$$

The equilibrium partial pressure of water in the galvanic cell is expressed by the Nernst equation:

$$E = RT/2F \cdot \ln[P_{H_2O}(P^r{}_{O_2})^{\tfrac{1}{2}} / P^r{}_{H_2O}(P_{O_2})^{\tfrac{1}{2}}] \qquad \text{Equation [3]}$$

$$P_{H_2O} = P^r{}_{H_2O}(P_{O_2}/P^r{}_{O_2})^{\tfrac{1}{2}} \exp(2EF/RT) \qquad \text{Equation [4]}$$

wherein $P^r{}_{H_2O}$ and $P^r{}_{O_2}$ represent the partial pressures of water and oxygen, respectively, at the reference electrode 26, E is the electromotive force of the electrolyte, F is the Faraday constant and R is the gas constant. Under ambient conditions, $P_{O_2}$ is assumed to be equal to $P^r{}_{O_2}$ and for sensing applications the partial pressure of water vapor in the sample gas, $P_{H_2O}$ can be estimated from the electromotive force of the cell in accordance with the following equations:

$$E = RT/2F \cdot \ln(P_{H_2O}/P^r{}_{H_2O})$$

$$P_{H_2O} = P^r{}_{H_2O} \cdot \exp(2EF/RT)$$

Figure 1C:
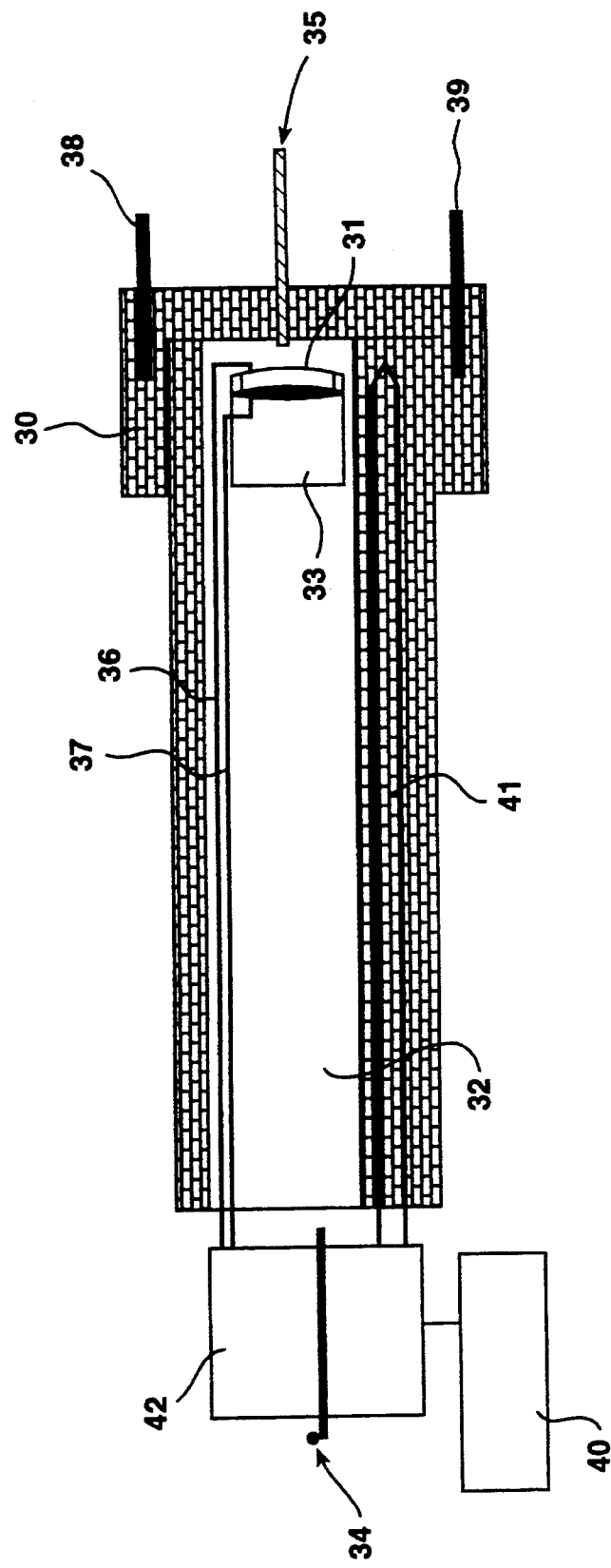
FIG. 1c is a front elevational view in cross section of a ceramic humidity probe in accordance with the invention.

With reference now to FIG. 1c, there is shown a front elevational view in cross-section of a ceramic humidity probe in accordance with the present invention. Shown is MACOR block 30 having a proton conducting solid electrolyte sensor 31 comprising a $HZr_2P_3O_{12}/ZrP_2O_7$ composite disposed in MACOR tube 32 and held in piece by means of an alumina ring 33. Conduits 34 and 35 are used for the introduction of reference and sample gases, respectively, into tube 32. Sensor 31 is connected to platinum leads 36 and 37. Also shown connected to block 30 are cartridge heaters 38 and 39. Output meter 40 is connected to signal processor 42 which is connected to platinum leads 36 and 37 and to a thermocouple 41 which is disposed in block 30.

In operation, block 30 is heated by means of heaters 38 and 39 and humidity is introduced through the reference and sample gas conduits 34 and 35, respectively, from a suitable source. Humidity is monitored by means of an output meter 40.

Figure 2:
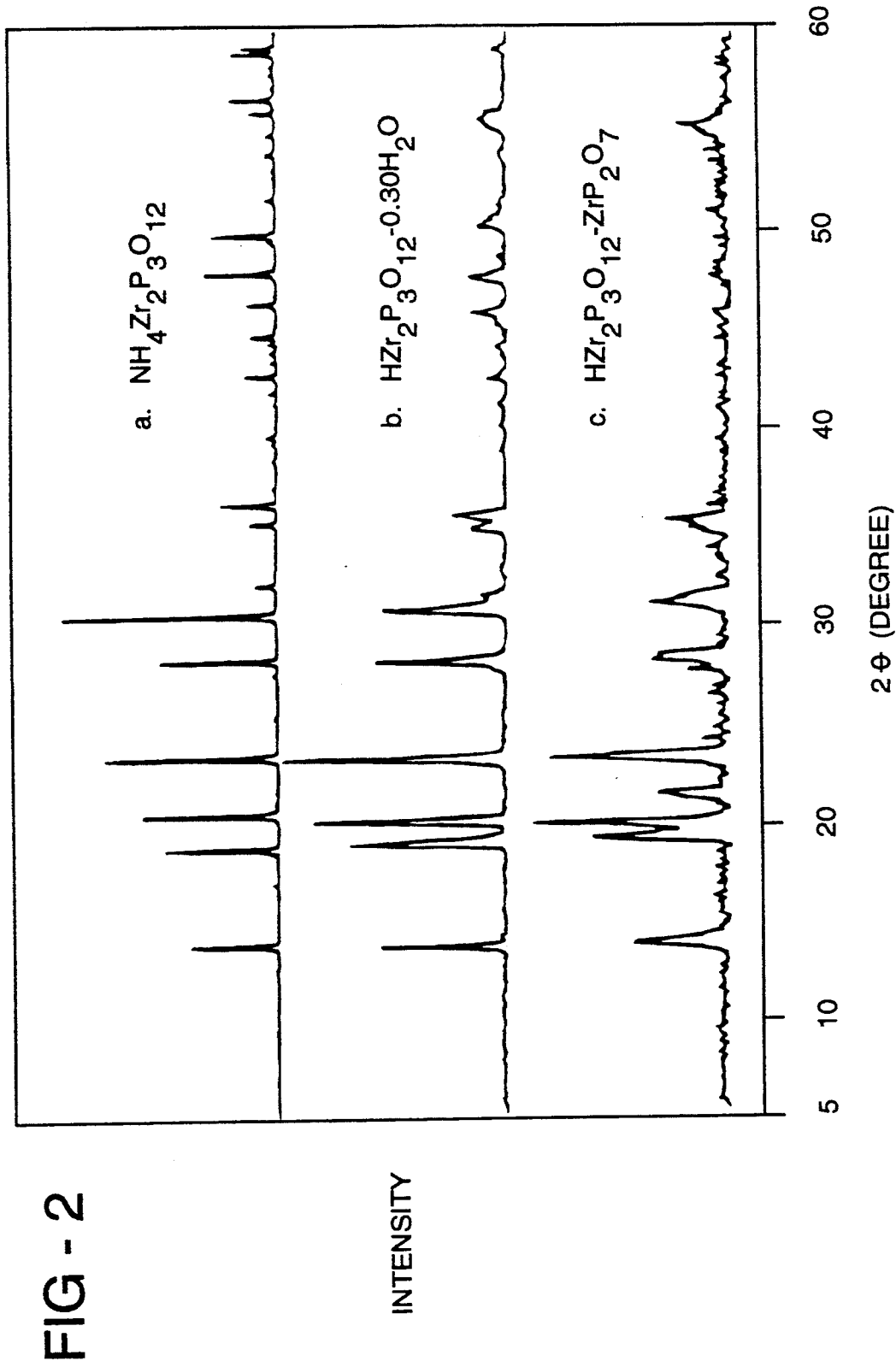
FIG. 2 is a graphical representation on coordinates of relative intensity against $2\theta$ in degrees showing x-ray diffraction patterns of (a) pure $(NH_4)Zr_2P_3O_{12}$, (b) $HZr_2P_3O_{12}$ and the sensor material $HZr_2P_3O_{12}/Zr_2P_2O_7$.

With reference now to FIG. 2, there is shown a graphical representation on coordinates of Intensity against $2\theta$ in degrees comparing x-ray diffraction patterns of $(NH_4)Zr_2P_3O_{12}$, $HZr_2P_3O_{12} \cdot 0.3H_2O$ and the $HZr_2P_3O_{12}/ZrP_2O_7$ composite sensor material of the invention. As noted in FIG. 2a, hydrothermally synthesized $(NH_4)Zr_2P_3O_{12}$ evidences high crystallinity and a structure identical with that of high temperature NASICON which evidences two polymorphs which are dependent upon calcination temperature. Below 600° C. a triclinic phase appears, and above 600° C. a rhombedral phase appears, the latter not undergoing a phase transition upon cooling or heating. Both phases respond to changes in humidity; however, the rhombohedral phase was used as the starting material for the sensor because of its stability at high temperature. The x-ray diffraction pattern of the sensor material of the invention (FIG. 2c) is identical with that of rhombohedral $HZr_2P_3O_{12}$ but for a few peaks attributable to $ZrP_2O_7$, thereby confirming the material as a composite of $HZr_2P_3O_{12}$ and $ZrP_2O_7$.

Figure 3:
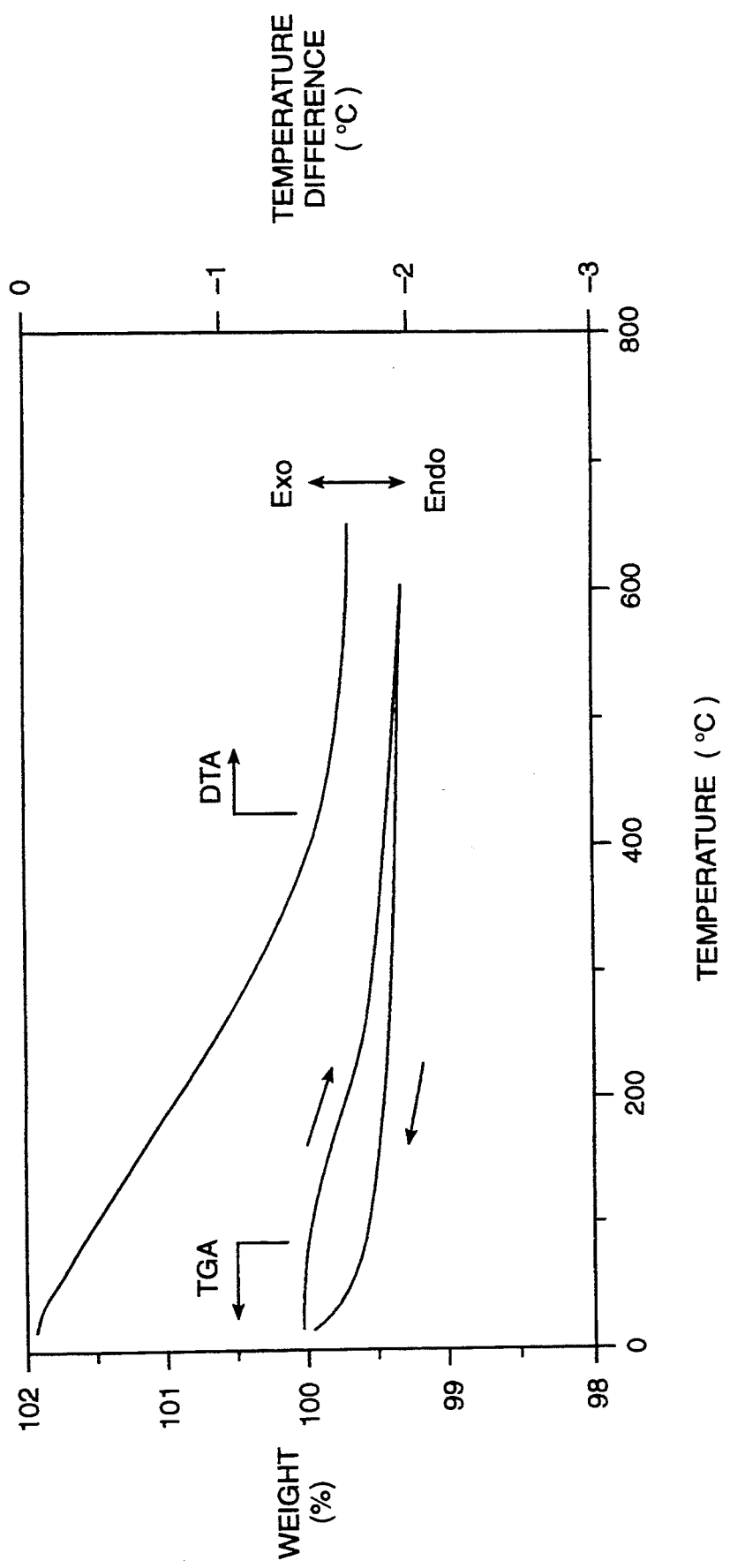
FIG. 3 is a graphical representation on coordinates of weight per cent against temperature in degrees Centigrade showing the DTA and TGA curves for the described sensor material.

With reference now to FIG. 3, the DTA and TGA curves for a sample of the sensor material of the invention is shown in graphical form on coordinates of weight against temperature in degrees centigrade. No phase change is evident over the temperature range (approximately 0°–600° C.), so indicating that the material is thermally stable during a heating/cooling cycle. It is noted that the DTA curve slopes smoothly during the entire period of heating, so indicating a gradual endotherm. The TGA heating curve reveals that upon heating a weight loss of approximately 0.75% occurs which is attributable to water loss which is absorbed by the sensor on exposure to air which corresponds with the formulation $HZr_2P_3O_{12} \cdot ZrP_2O_7 \cdot 0.15H_2O$. The TGA cooling curve for the same sample evidenced a weight gain beginning at approximately 400° C. due to absorption of water at relatively low temperature.

Figure 4:
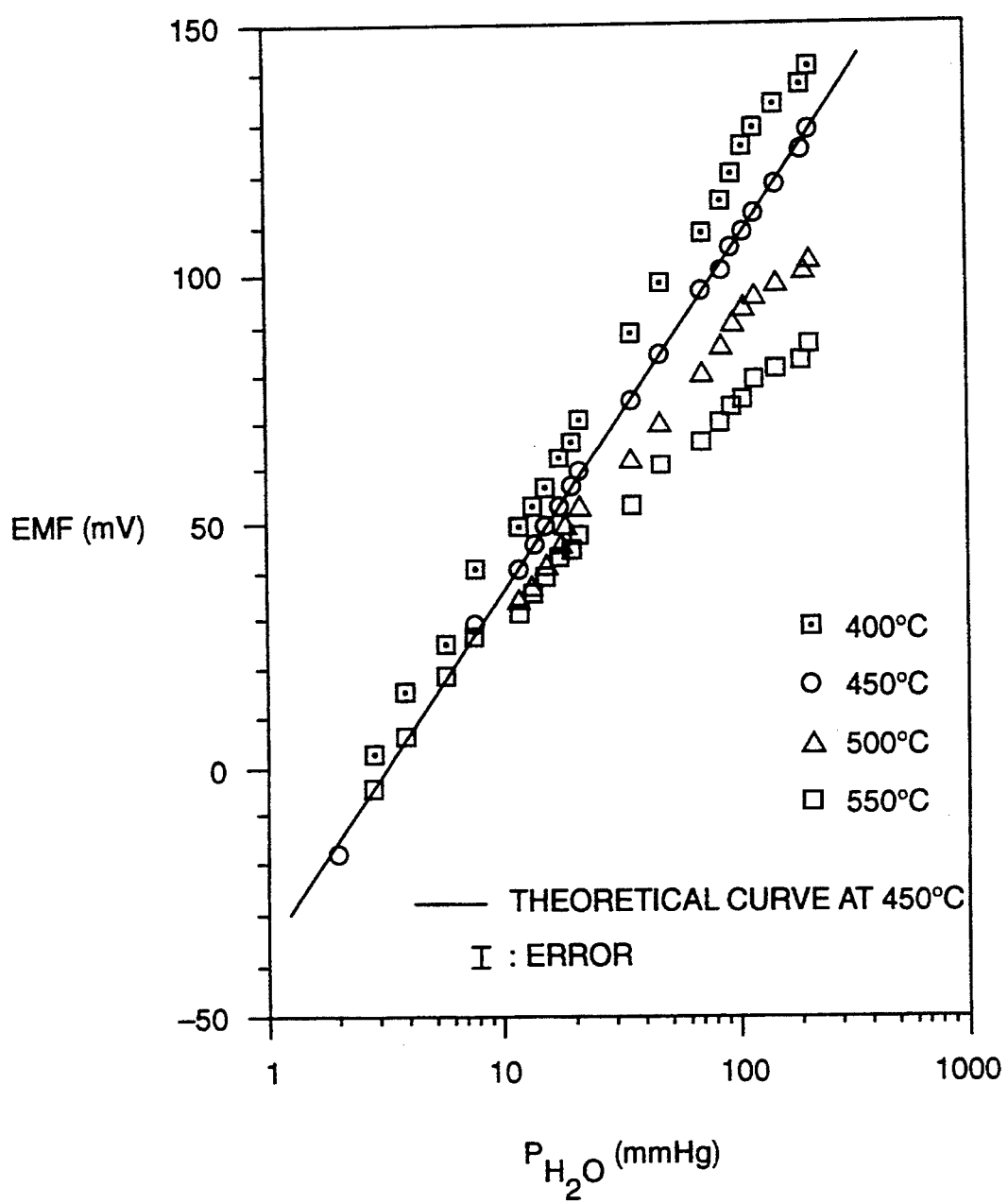
FIG. 4 is a graphical representation on coordinates of electromotive force in millivolts against water vapor pressure, P in mmHg, showing the humidity dependence of electromotive force of the sensor at 400°, 450°, 480°, 500° and 550° C. respectively.

With reference now to FIG. 4, there is shown the electromotive force (EMF) response of the galvanic cell as a function of the log of the partial pressure of water in the sample compartment at a temperature within the range of 400°–550° C. The figure reveals that at temperatures less than 450° C. the EMF values are higher and at temperatures greater than 450° C. the EMF values are lower than expected from the Nernst equation and are non-linear. This voltage variation at the lower temperatures is attributed to absorption of water on the surface of the sensor disk which is confirmed by the TGA cooling curve shown in FIG. 3.

Figure 5:
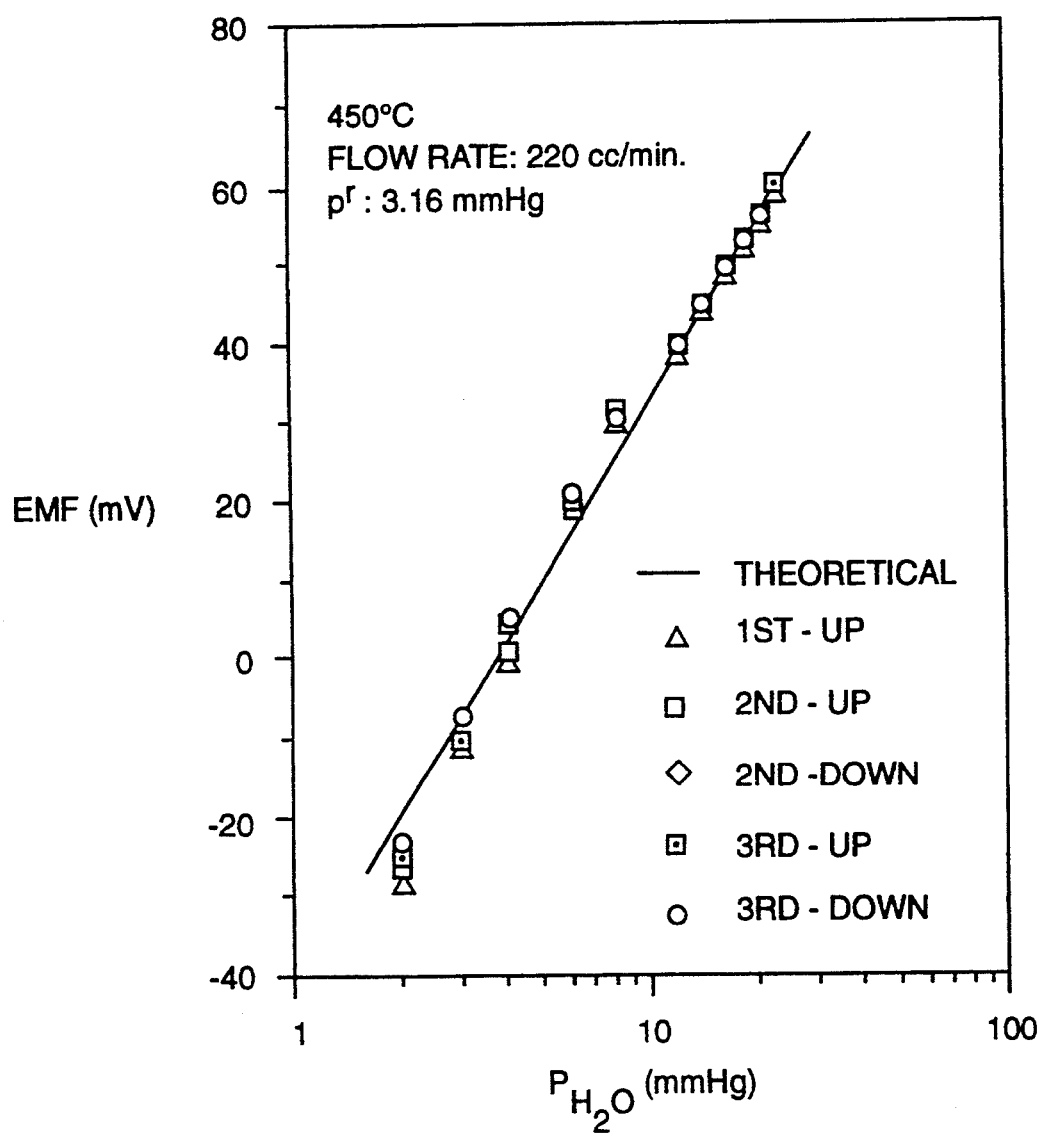
FIG. 5 is a graphical representation on coordinates of electromotive force in millivolts against water vapor pressure, P, in mmHg showing the humidity dependence of electromotive force (EMF) of the sensor of the invention at 450° C. showing cycling data.

The conduction characteristics of the sensor material were also studied using a wet oxygen concentration cell having the same partial pressure of water vapor in both the sample and reference compartments. The partial pressures of oxygen in both the sample and reference compartments were adjusted from 68 to 745 mmHg with helium used as a balancing gas. The measured EMFs at 450° C. of the wet oxygen concentration cell with changing oxygen concentration shown in FIG. 5 follow the theoretical values calculated from Equation 3. This confirms that the described sensor operates in the cell by a mechanism conforming to the Equations, 1 and 2.

A similar experiment performed in a wet hydrogen concentration cell evidenced Nernstian behavior as a function of the ratio of hydrogen partial pressure in the reference and sample compartments ($H_2{}^r/H_2{}^s$). This indicated that under the appropriate wet conditions in both chambers, the device will operate as an oxygen sensor.

Figure 6:
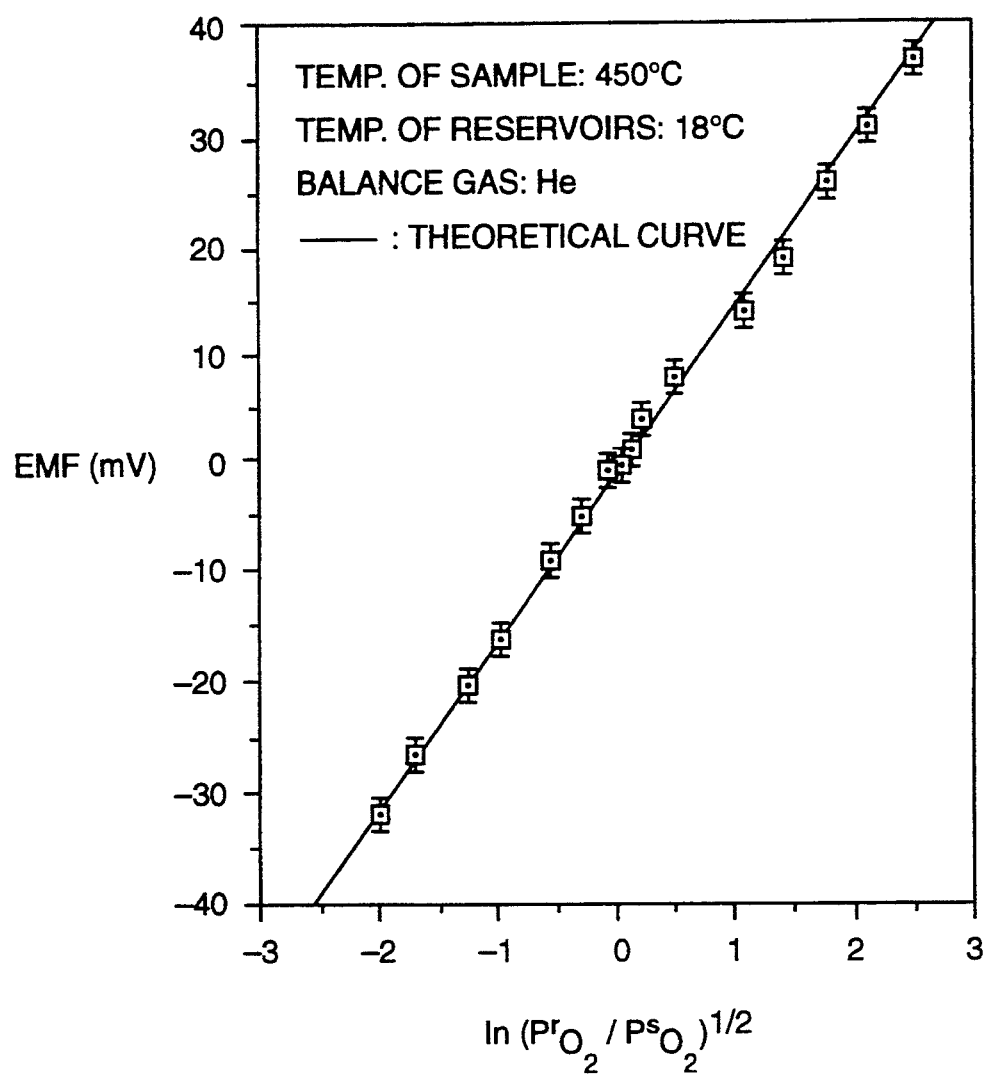
FIG. 6 is a graphical representation on coordinates of EMF in millivolts against the ratio of partial oxygen pressures in the reference and sample compartments showing conduction characteristics of the sensor material.

FIG. 6 is a graphical representation on coordinates of electromotive force (EMF) in millivolts against the ratio of the partial pressure of oxygen in the reference and sample compartments. This figure is indicative of the conduction characteristics of the sensor material. A wet oxygen concentration cell with the same partial pressures of water vapor in both the sample and reference compartments was employed. Pressures in these compartments were adjusted with a helium balance gas from 68–745 mmHg. At 450°, the measured electromotive forces of the wet oxygen concentration cell with changing oxygen concentration follow the theoretical values calculated from Equation 3 and noted by reference to FIG. 6, so confirming that the sensor material operates by a mechanism in accordance with Equations 1 and 2.

Figure 7A:
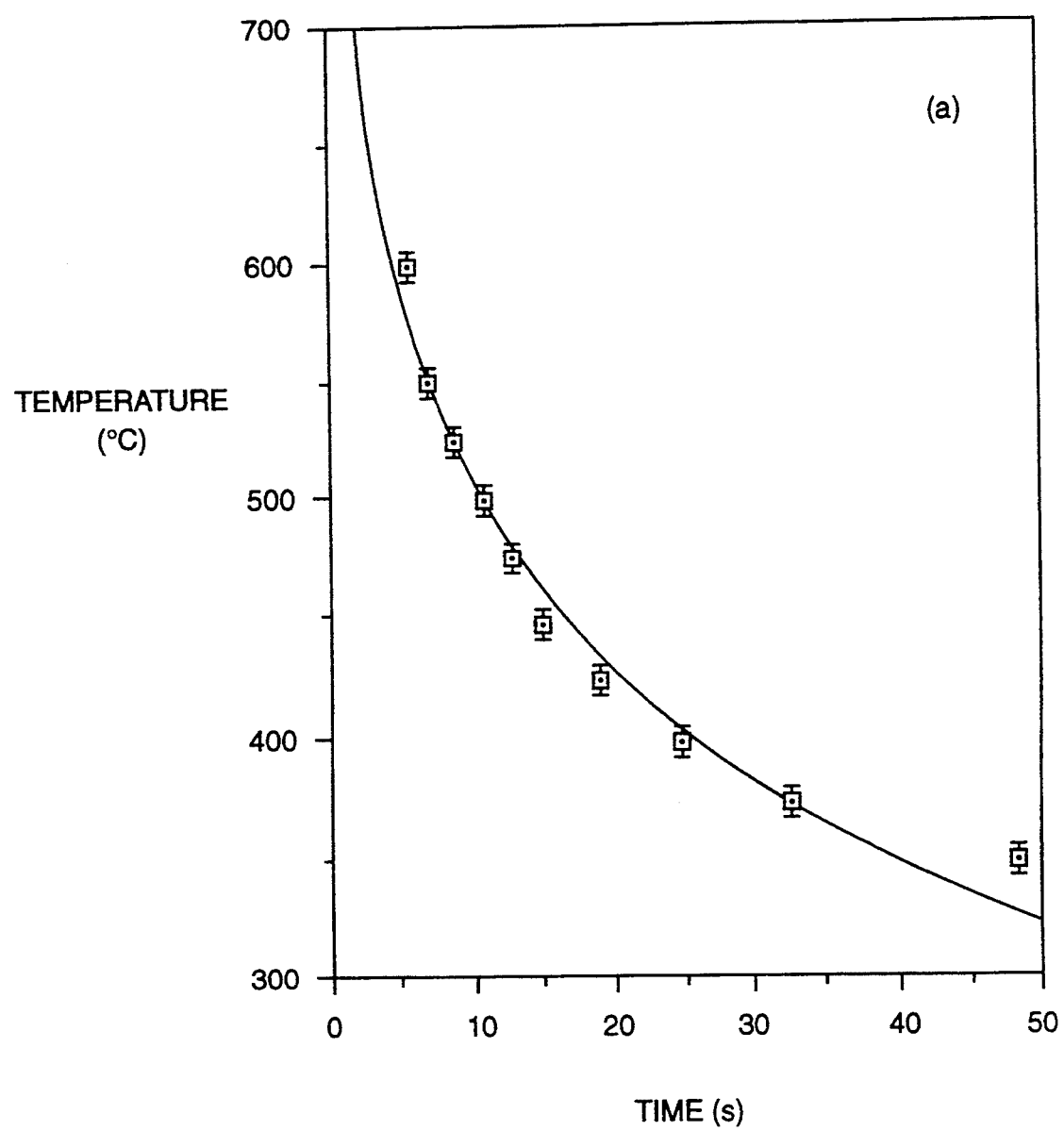
FIG. 7a is a graphical representation on coordinates of temperature in degrees Centigrade against time in seconds showing the temperature dependence of the response time for the humidity sensor with a change of partial pressure of water from 6–8 mmHg.
Figure 7B:
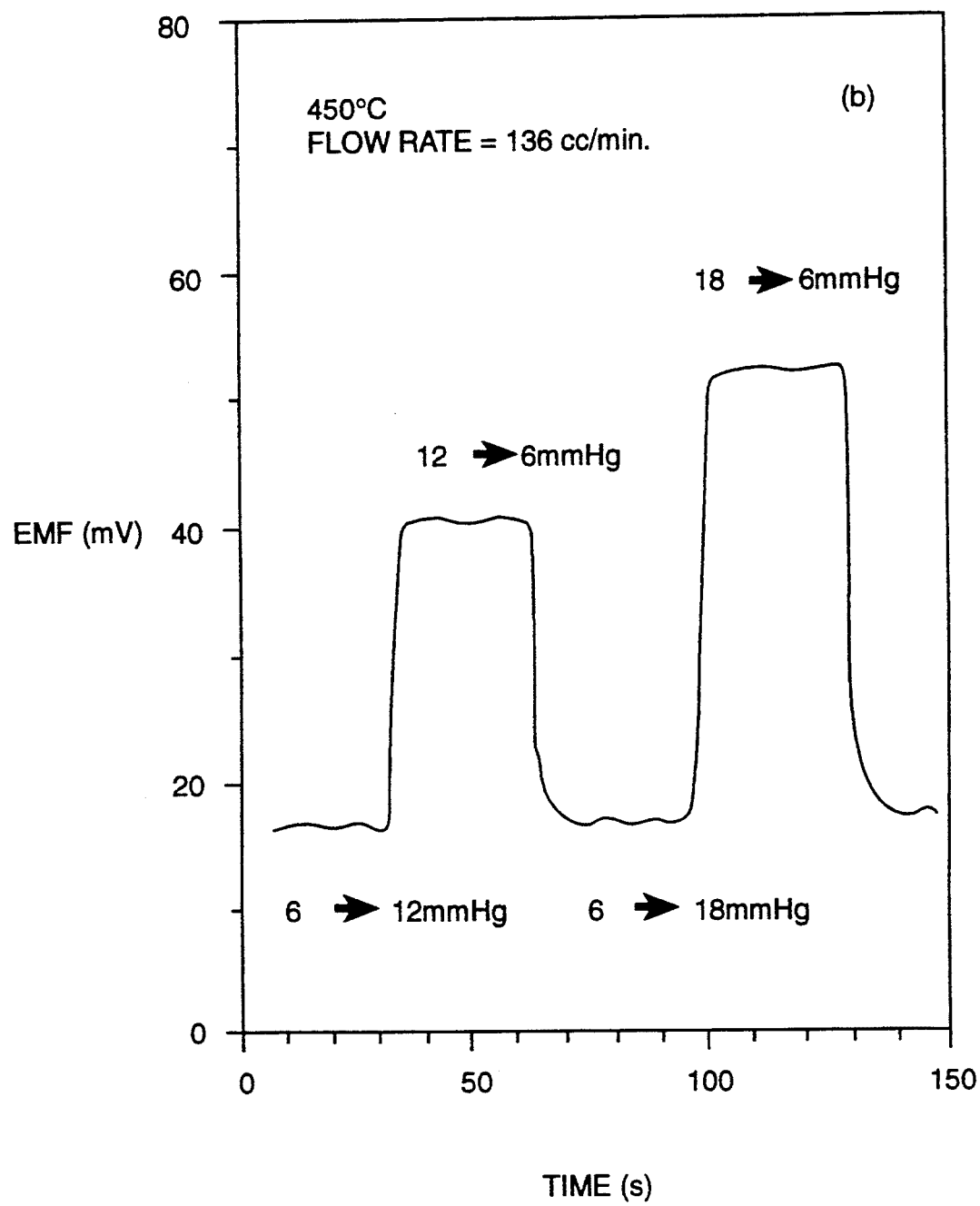
FIG. 7b is a graphical representation on coordinates of electromotive force against time in seconds showing the variation of electromotive force with time for the same cell as shown in FIG. 7a with partial pressure changes ranging from 6–12 mmHg and 6 to 18 mmHg at 450° C.

The response time of the sensor as a function of temperature on changing water vapor pressure is shown in FIG. 7a. As the humidity varies, the EMF responds rapidly and reaches a steady state within a few seconds at all temperatures studied. At 350° C., the response time was 48 seconds. However, at elevated temperatures, for example 450° C., the response time was only 15 seconds, as noted in FIG. 7b.

The effect of selected impurity gases in the water vapor was also studied. Thus, for example, ethyl alcohol, acetic acid and ammonia were introduced to the system and the EMF of the sensor evaluated. Pure ethyl alcohol, acetic acid and ammonia, respectively, were mixed with water in a volume ratio of 100 ppm or 1000 pm. The solution mixture served as the source of saturated water vapor plus impurity vapor supplied to the sample compartment. The sensor material was found to be stable with respect to each of the impurity gasses and humidity sensing was not affected within the experimental error of measurement for 100 ppm impurity gas concentration. This evidences the selectivity of the sensor. As the concentration of impurity gas increased beyond 100 ppm, the EMF value also increased. At this temperature, the EMF appears to be dependent upon the ethyl alcohol concentration at values greater than 100 ppm. This phenomenon is attributed to proton reactivity of the ethyl alcohol molecules which are absorbed on the surface of the sensor disk in the sample compartment which provides additional protons and enhanced EMF, so suggesting the use of the humidity sensor as a proton-containing gas sensor and/or catalyst.

While the invention has been described in detail in the foregoing specification and the exemplary embodiments have been alluded to for purposes of illustration, it will be understood by those skilled in the art that such has been solely for purposes of exposition only and are not to be construed as limiting.

What is claimed is:

1. A galvanic cell humidity sensor comprising a proton conducting solid electrolyte composite of $HZr_2P_3O_{12}$ and $ZrP_2O_7$.

2. The sensor in accordance with claim 1 further comprising a pair of electrodes affixed to the proton conducting solid electrolyte.

3. A galvanic cell assembly for sensing humidity including a proton conducting solid electrolyte comprising a composite of $HZr_2P_3O_{12}$ and $ZrP_2O_7$ having a pair of electrodes affixed thereto, said electrolyte being disposed in a housing, said electrolyte separating the cell into a reference gas chamber and a sample gas chamber.

4. A ceramic humidity probe for sensing humidity including a proton conducting solid electrolyte comprising a composite of $HZr_2P_3O_{12}$ and $ZrP_2O_7$ having a pair of electrodes affixed thereto, said electrolyte being disposed in a ceramic housing having means for introducing sample and reference gases and means for monitoring the humidity in said housing.

5. A galvanic cell humidity sensor comprising:
a housing having first and second ends;
a proton conducting solid electrolyte comprising a composite of $HZr_2P_3O_{12}$ and $ZrP_2O_7$ disposed at the first end of the housing, the solid electrolyte formed in the shape of a disk having opposing faces;
support means disposed within the first end of the housing for supporting the solid electrolyte within the housing;
electrodes disposed on the opposing faces of the electrolyte;
leads attached to the electrodes, the leads extending through the second end of the housing;
a signal processor for receiving the leads;
a thermocouple positioned adjacent the housing, the thermocouple interconnected with the signal processor;
heater means positioned adjacent the first end of the housing for heating the solid electrolyte;
a sample gas conduit extending through the first end of the housing to the solid electrolyte for permitting a sample gas to be introduced within the housing;
a reference gas conduit for introducing a reference gas within the housing; and
an output meter for monitoring humidity.

6. The sensor of claim 5 wherein the humidity sensor operates in the temperature range of 350° C. to 600° C.

7. The sensor of claim 5 wherein the humidity sensor operates at approximately 450° C.

8. A galvanic cell assembly for measuring humidity comprising:
a housing;
a proton conducting solid electrolyte comprising a composite of $HZr_2P_3O_{12}$ and $ZrP_2O_7$ disposed in the housing;
a signal processor on the exterior of the housing;
a pair of electrodes fixed to the solid electrolyte;
a pair of leads extending from the electrodes to the signal processor;
a reference gas chamber; and
a sample gas chamber for introducing a sample gas into the housing;
wherein the signal processor measures the difference in humidity of a sample gas and a reference gas.

9. The assembly of claim 8 further including heater means for heating the solid electrolyte to a high temperature.

10. The assembly of claim 9 wherein the sensor operates in the temperature range of 350° C. and 600° C.

11. The assembly of claim 9 wherein the humidity sensor operates at approximately 450° C.

12. A galvanic cell assembly for sensing humidity at high temperatures comprising:
a housing comprising a tubing;
a proton conducting solid electrolyte comprising a composite of $HZr_2P_3O_{12}$ and $ZrP_2O_7$ positioned within the housing;
sealant means for holding the proton conducting solid electrolyte within the housing;
first and second chambers formed at each side of the solid electrolyte within the housing;
a reference gas introduced into the first chamber;
a sample gas introduced into the second chamber;
an electrode formed on each side of the proton conducting solid electrolyte;
leads extending from the electrodes to the exterior of the housing; and
a signal processor for receiving the leads and comparing humidity of a sample gas with a reference gas.

13. The assembly of claim 13 disposed within an electric furnace for operation at a high temperature.

14. The assembly of claim 13 wherein the reference chamber is fixed at 3.16 mmHg.

* * * * *